United States Patent
Sakamoto

[11] Patent Number: 6,017,311
[45] Date of Patent: Jan. 25, 2000

[54] ULTRASOUND PROBE HAVING AN INSULATING SLEEVE MEMBER

[75] Inventor: Toshio Sakamoto, Omiya, Japan

[73] Assignee: Fuji Photo Optical Co., Ltd., Omiya, Japan

[21] Appl. No.: 09/158,284

[22] Filed: Sep. 22, 1998

[30] Foreign Application Priority Data

Sep. 24, 1997 [JP] Japan .................................. 9-274945

[51] Int. Cl.[7] ........................................ A61B 8/12
[52] U.S. Cl. ...................... 600/459; 600/462; 600/466; 606/46
[58] Field of Search .................... 600/445, 459, 600/462, 472, 446, 463, 109, 117; 606/130, 1, 46; 128/908; 73/623; 347/75

[56] References Cited

U.S. PATENT DOCUMENTS

| | | | |
|---|---|---|---|
| 4,034,744 | 7/1977 | Goldberg | 600/445 |
| 4,370,662 | 1/1983 | Hou et al. | 347/75 |
| 4,523,470 | 6/1985 | Muller et al. | 73/623 |
| 4,565,724 | 1/1986 | Silwa, Jr. et al. | 600/459 |
| 5,211,176 | 5/1993 | Ishiguro et al. | 600/459 |
| 5,368,037 | 11/1994 | Eberle et al. | 600/463 |
| 5,377,682 | 1/1995 | Ueno et al. | 600/466 |
| 5,417,216 | 5/1995 | Tanaka | 600/463 |
| 5,596,991 | 1/1997 | Tanaka | 600/462 |

*Primary Examiner*—Marvin M. Lateef
*Assistant Examiner*—Ali M. Imam
*Attorney, Agent, or Firm*—Oblon, Spivak, McClelland, Maier & Neustadt, P.C.

[57] ABSTRACT

An ultrasound probe of the type having, successively from its head to tail end, an ultrasound scanner head assembly accommodating an ultrasound transducer element rotatably within an end cap, an elongated flexible cord having a flexible transmission shaft of tightly wound metal wire coils within an outer sheathing tube, and a tail end connector. The ultrasound probe is characterized by a joint construction for the ultrasound scanner head, including: a metallic joint member axially extended from the end cap of the ultrasound scanner head assembly on the proximal side thereof and joining the ultrasound scanner head with an outer sheathing tube of the flexible cord by fitting engagement therewith; a cylindrical rotating member located internally of the joint member and the outer sheathing tube, and connecting a fore end portion of the flexible transmission shaft with a rotary support member of the ultrasound transducer element at a position axially on the proximal side of a rear end of the joint member; and an insulating sleeve member fitted on the cylindrical rotating member and keeping the cylindrical rotating member out of contact with the metallic joint member for electrical insulation purposes.

4 Claims, 6 Drawing Sheets

ULTRASOUND PROBE HAVING AN INSULATING SLEEVE MEMBER

FIELD OF THE ART

This invention relates to an ultrasound probe of the sort which has an ultrasound transducer element rotatably incorporated into a housing of an ultrasound scanner head assembly at the distal end of an elongated flexible cord in such a way that the ultrasound transducer element can be put in rotation by remote control.

PRIOR ART

By scan mode, the ultrasound probes currently in use in medical fields for examination of internal body tissues can be categorized into a linear scan type which is arranged to make a linear scan with an ultrasound transducer element moving in a linear direction, and a radial scan type which is arranged to make a radial scan with an ultrasound transducer element put in a rotational movement. Further, by location of scanner head in examination, the ultrasound probes can be categorized into an insertion type which is designed to be introduced into a body cavity for making a scan through an intracavitary wall, and an non-insertion type which is designed to make a scan from outside a patient's body through the skin layer. Recently, the insertion type ultrasound probes which can transmit and receive ultrasound signals from the proximity of a diseased portion are employed more widely than the non-insertion type which are inevitably influenced by subcutaneous fat.

In guiding an insertion type ultrasound probe into a body cavity, it becomes necessary to check out the position of a scanner head at the distal end of the ultrasound probe. This is usually done by employing an ultrasound endoscope incorporating an ultrasound scanner integrally into an endoscope or by checking out the scanner position by way of an X-ray image. Further, the insertion type includes an endoscopically inserting ultrasound probe which uses an endoscope as a guide means at the time of introduction into a body cavity, so that internal body tissues can be examined by ultrasound scanning in addition to an endoscopic examination.

In case an endoscope is used as a guide means, an ultrasound probe is placed in a biopsy channel which is normally used for introduction of a bioptic or surgical instrument like forceps. Therefore, in the case of an endoscopically inserting ultrasound probe, an ultrasound scanner head assembly with an ultrasound transducer element is connected to a distal end of an elongated flexible cord. The ultrasound transducer element needs to be put in rotation at the time of a radial scan. In this regard, in order to comply with downsizing requirements, it has been the usual practice to drive the ultrasound transducer element by remote control instead of mounting a rotational drive means on the scanner head assembly. More specifically, the ultrasound transducer element is supported on a rotary member which is in turn rotatably supported within a closed end cap of the ultrasound scanner head assembly. From the standpoint of acoustic characteristics, the end cap is formed of silicon resin, polyethylene or other synthetic resins with satisfactory acoustic characteristics. For rotationally driving the rotary member, a flexible transmission shaft is fitted in an outer sheathing tube of the flexible cord. The outer tube is connected to the end cap of the scanner head assembly while the flexible transmission shaft is connected to the rotary member to rotate the ultrasound transducer element with the rotary member as the flexible shaft is turned about its longitudinal axis within the outer tube. A signal cable from the ultrasound transducer element is passed internally through the flexible transmission shaft. As for the flexible transmission shaft which can internally provides a passage for the signal cable, it is preferable to employ a tightly wound metal wire tube.

The ultrasound probe, with the construction as described above, is connected to an ultrasound image observation terminal which controls transmission and reception of ultrasound signals, and, for display on a monitor screen, generates ultrasound images by processing return echo signals from the ultrasound transducer element. An ultrasound examination system of this sort further includes a drive means for rotationally driving the ultrasound transducer element through the flexible transmission shaft, and an angle detection means for detecting the rotational angle of the transducer element. The rotational drive means and angle detection means may be provided on the ultrasound image observation terminal. However, in order to permit common use of the ultrasound observation terminal, it is preferable to connect the ultrasound probe detachably to a probe control unit or probe controller with such rotational drive means and angle detection means.

The ultrasound probe may be inseparably connected to the probe controller if desired. However, taking into the maneuverability in operation and convenience in handling into consideration, it is the general practice to connect the ultrasound probe disconnectibly to the probe controller. Accordingly, the probe controller contains mechanisms for the rotational drive and angle detection and at the same time functions as a signal relay between the ultrasound transducer element and the ultrasound image observation terminal. In order to connect the ultrasound probe disconnectibly to the probe controller, a tail end connector is provided at the proximal end of the flexible cord. Thus, generally speaking, an endoscopically inserting ultrasound probe is largely constituted by an ultrasound probe, a probe controller and an ultrasound image observation terminal which are disconnectibly connected with each other.

The ultrasound probe, to be introduced into a patient's body, should be constructed to preclude the possibilities of electric current from flowing into the patient body from any part of the probe. In this regard, the tail end connector which is provided at the proximal end of the probe for disconnectibly coupling same with the probe controller usually has electrodes in an exposed state to serve as signal relay means in cooperation with corresponding electrodes on the part of the probe controller. For example, in case of a single-element ultrasound transducer, a pair of electrodes are provided on a rotating side of the tail end connector. The flexible transmission shaft which is provided coextensively in the flexible cord of the probe is constituted by conductive metal wires, so that electric current would flow through the flexible shaft should it come into contact with an electrode.

Since the flexible transmission shaft is connected to the rotary support member of the ultrasound transducer element as mentioned hereinbefore, the ultrasound scanner head has to be electrically insulated at least in these portions which support the ultrasound transducer element. For this reason, a rotary base which directly supports the ultrasound transducer element is formed of an electrically insulating material. However, the rotary base needs to be connected to a fore end portion of the flexible transmission shaft through a rotating ring in the form of a rigid metal pipe or the like to ensure smooth and accurate transmission of rotation and to increase the strength of coupling portions. The rotating ring has one end thereof securely fixed to the rotary base by means of screws or other fixation means, and the other end welded or brazed to the flexible transmission shaft.

On the other hand, the outer tube, which sheathes the flexible transmission shaft, is connected to the end cap of the ultrasound scanner head assembly. The outer tube is formed of a soft and flexible material, while the end cap is formed of a synthetic resin material which is relatively thin in wall thickness. Since it is difficult to connect the outer tube directly to the end cap, a rigid connecting member is interposed between these two members. This connecting member has a front joint portion to be connected with the end cap of the ultrasound scanner head assembly and a rear joint portion to be connected with the outer sheathing tube of the flexible cord. The connecting member also serves as a shape retainer for the end cap which has a thin-wall structure. Accordingly, the connecting member is exposed to the outside and brought into contact with intracavitary walls at the time of ultrasound scanning operations. Consequently, when the ultrasound transducer element is put in rotation through the flexible transmission shaft for an ultrasound scan, current can flow into the patient's body if a contact is made between the connecting member and the flexible transmission shaft or the rotating ring.

For these reasons, it is necessary to electrically insulate the flexible transmission shaft from the electrodes of the tail end connector. At a proximal end, the flexible transmission shaft is connected to a cylindrical rotating member of the tail end connector, which is provided with a pair of electrodes. In connecting the proximal end of the flexible shaft with a rotating member of the connector, a metal member is employed to form a strong joint by welding or similar joint method. Therefore, in order to prevent electric current from flowing to the patient's body through the flexible shaft, rotating ring and connecting member, it is necessary to provide electrical insulation means between the connecting member of the flexible transmission shaft and the electrodes on the part of the rotating ring of the tail end connector. For this purpose, the tail end connector of the probe should include an insulator between a member to be connected with the flexible transmission shaft and one of its two electrodes, in addition to an insulator which insulates the two electrodes of the connector from each other. Accordingly, at least the tail end connector needs to be composed of a member for connection to the flexible transmission shaft, a first insulation member, a first electrode, a second insulation member and a second electrode. However, two insulation members in two different positions would result in a connector which is too lengthy in the axial direction and inferior in strength. Especially, since the electrodes of the connector are exposed to the outside, it is very likely that the connector will suffer from fracturing or other damages when external forces are exerted thereon.

SUMMARY OF THE INVENTION

In view of the foregoing situations, it is an object of the present invention to provide an ultrasound probe which is arranged to insulate a metallic joint member of an ultrasound scanner head from electrodes of a tail end connector of the probe in an assured manner without degrading the strength of the tail end connector.

It is another object of the present invention to provide an ultrasound probe which has an outer sheathing tube of a flexible cord of the probe connected to an end cap of the ultrasound scanner head through a joint construction of increased strength including a metallic joint ring which is electrically insulated in an assured manner from a flexible transmission shaft fitted in the outer sheathing tube.

It is still another object of the present invention to provide an endoscopically inserting ultrasound probe having, at the distal end of a flexible cord, a bulky ultrasound scanner head larger than the inside diameter of an endoscopic biopsy channel, and having the ultrasound scanner head securely connected to the flexible cord through a joint construction which is increased in strength and which can securely prevent leaks of electric current to the outside through exterior surfaces of the ultrasound scanner head.

In accordance with the present invention, the above-stated objectives are achieved by the provision of an ultrasound probe of the type having, successively from its head to tail end thereof, an ultrasound scanner head assembly accommodating an ultrasound transducer element rotatably within an end cap, an elongated flexible cord having a flexible transmission shaft of tightly wound metal wire coils within an outer sheathing tube, and a tail end connector. The ultrasound probe according to the present invention is characterized by the provision of: a metallic joint member axially extended from the end cap of the ultrasound scanner head assembly on the proximal side thereof and joining the ultrasound scanner head with a fore end portion of the outer sheathing tube of the flexible cord by fitting engagement therewith; a cylindrical rotating member located internally of the joint member and the outer sheathing tube, and connecting a fore end portion of the flexible transmission shaft with a rotary support member of the ultrasound transducer element at a position axially on the proximal side of a rear end of the joint member; and an insulating sleeve member fitted on the cylindrical rotating member and keeping the cylindrical rotating member out of contact with the metallic joint member for electrical insulation purposes.

In this instance, the ultrasound probe alone can be introduced into a body cavity. Alternatively, it may be introduced into a body cavity by way of a biopsy channel which is provided in an endoscopic insertion instrument. In the case of an endoscopically inserting ultrasound probe, the ultrasound transducer element on the scanner head is preferred to be of a relatively large size which can enhance the efficiency of ultrasound examination. When the ultrasound scanner head employs a large transducer element, however, it could become too bulky to pass through a narrow biopsy channel on an endoscope. In such a case, however, the ultrasound probe can be placed in an endoscopic biopsy channel not from the bulky scanner head assembly but from the tail end connector and flexible cord which are formed in thinner and narrower shapes as compared with the endoscopic biopsy channel. A tail end connector of a thin and narrow shape however is normally fragile and difficult to find spaces for incorporating extra members which are usually required for electrical insulation purposes. On the other hand, the ultrasound scanner head which is not required to pass through the endoscopic biopsy channel can an inflexible rigid portion over a substantial length at its joint portion with the flexible cord. Accordingly, when the ultrasound probe is placed in a biopsy channel of an endoscopic insertion instrument with the ultrasound scanner head projected from the distal end of the biopsy channel, a probe portion which remains in a rigid tip end section of the endoscopic insertion instrument can be utilized as a joint portion for connecting the ultrasound scanner head securely with the flexible cord by fitting engagement therewith over a substantial length.

The above and other objects, features and advantages of the invention will become apparent from the following description, taken in conjunction with the accompanying drawings. Needless to say, the drawings show by way of example one preferred embodiment of the invention and should not be construed as being presented in a limitative sense.

DESCRIPTION OF PREFERRED EMBODIMENTS

Figure 1:
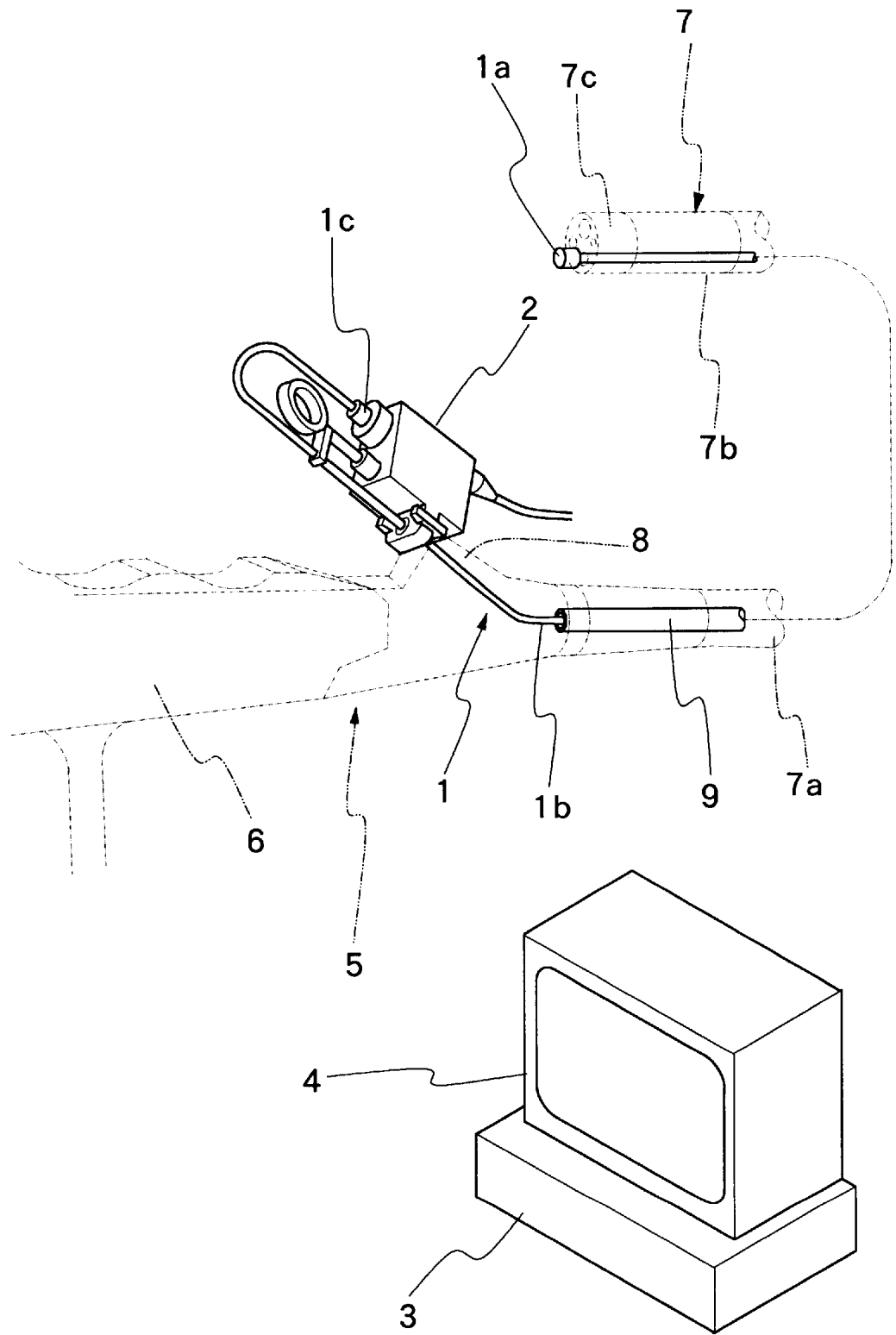
FIG. 1 is a schematic illustration of the general layout of an ultrasound examination system employing an ultrasound probe according to the present invention.

Hereafter, the present invention is described more particularly by way of its preferred embodiment shown in the drawings. In the following description of a preferred embodiment, the present invention is explained by way of an ultrasound probe of endoscopically inserting type which is arranged to be introduced into a body cavity through an endoscopic biopsy channel, more particularly, by way of an endoscopically inserting ultrasound probe having an ultrasound scanner head which is so bulky as to necessitate to place the probe in an endoscopic insertion instrument before inserting the endoscope into a patient's body.

Referring first to FIG. 1, there is shown a general layout of an ultrasound examination system, which is largely constituted by an ultrasound probe 1, a probe controller 2 and an ultrasound image observation terminal 3 with a monitor screen 4. The ultrasound probe 1 is introduced into a body cavity through an endoscope 5. In this instance, the endoscope 5 is of the type which has an insertion instrument 7 extended out of a manipulating head grip 6. The endoscopic insertion instrument 7 is provided with a flexible section 7a which occupies a major part of the insertion instrument 7 in length. Connected to the fore end of the flexible section 7a is an angle section 7b which can be bent toward an arbitrary direction, and connected to the fore end of the angle section 7b is a rigid tip end section 7c which has a predetermined length in the axial direction to accommodate an endoscopic image pickup means, for example, such as objective lens, solid-state image sensor and the like. Through an entrance housing 8 which is provided on the manipulating head grip 6 of the endoscope 5, the ultrasound probe 1 is inserted into a biopsy channel 9 which is provided internally of and over the entire length of the endoscopic insertion instrument 7. The endoscopic biopsy channel 9 is provided with an exit opening on the distal end face of the rigid tip end section 7c of the endoscopic insertion instrument 7. When placed in the endoscopic biopsy channel 9, the ultrasound scanner head 1a is projected on the front side of the rigid tip end section 7c of the endoscopic insertion instrument 7.

Figure 2:
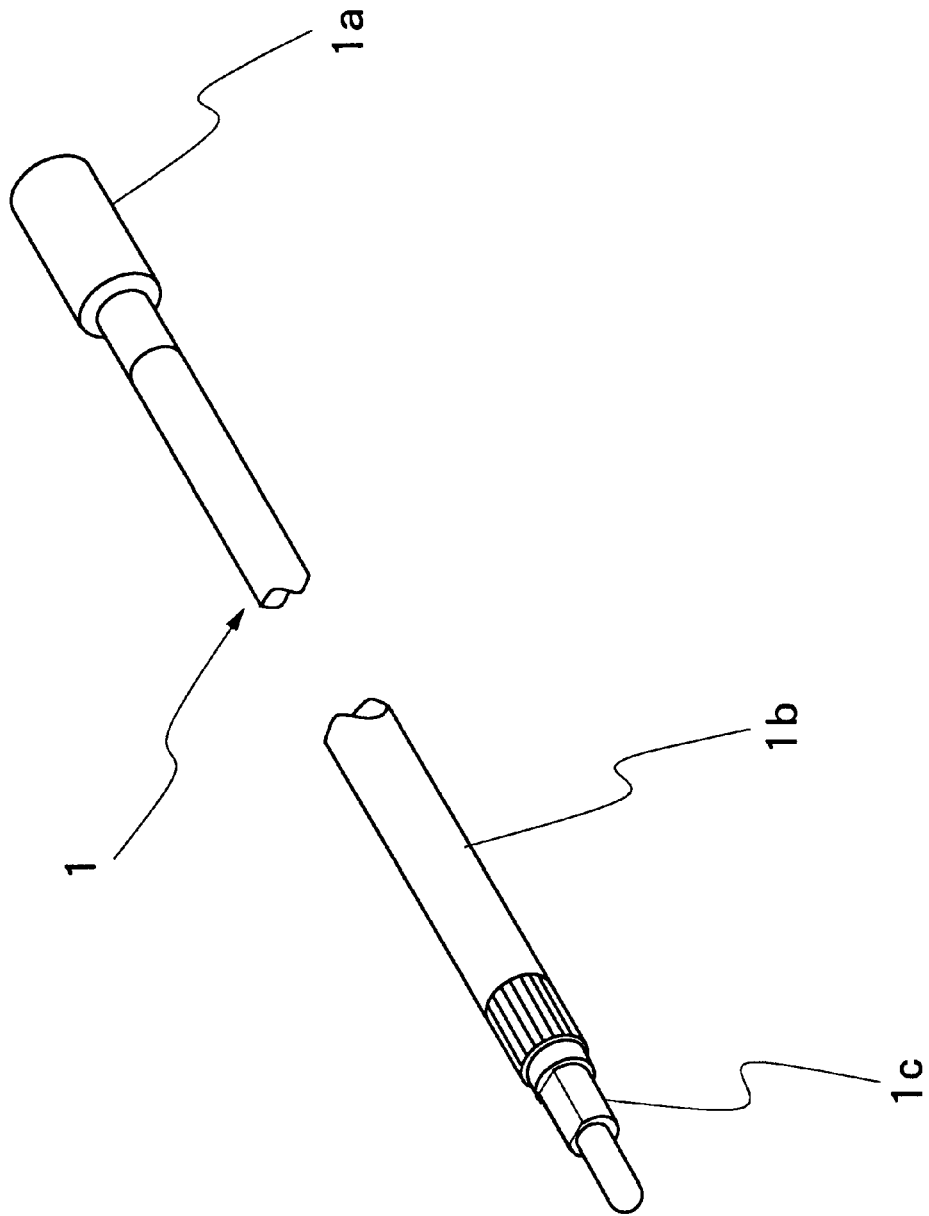
FIG. 2 is an outer view of the ultrasound probe and a coupling adaptor.
Figure 3:
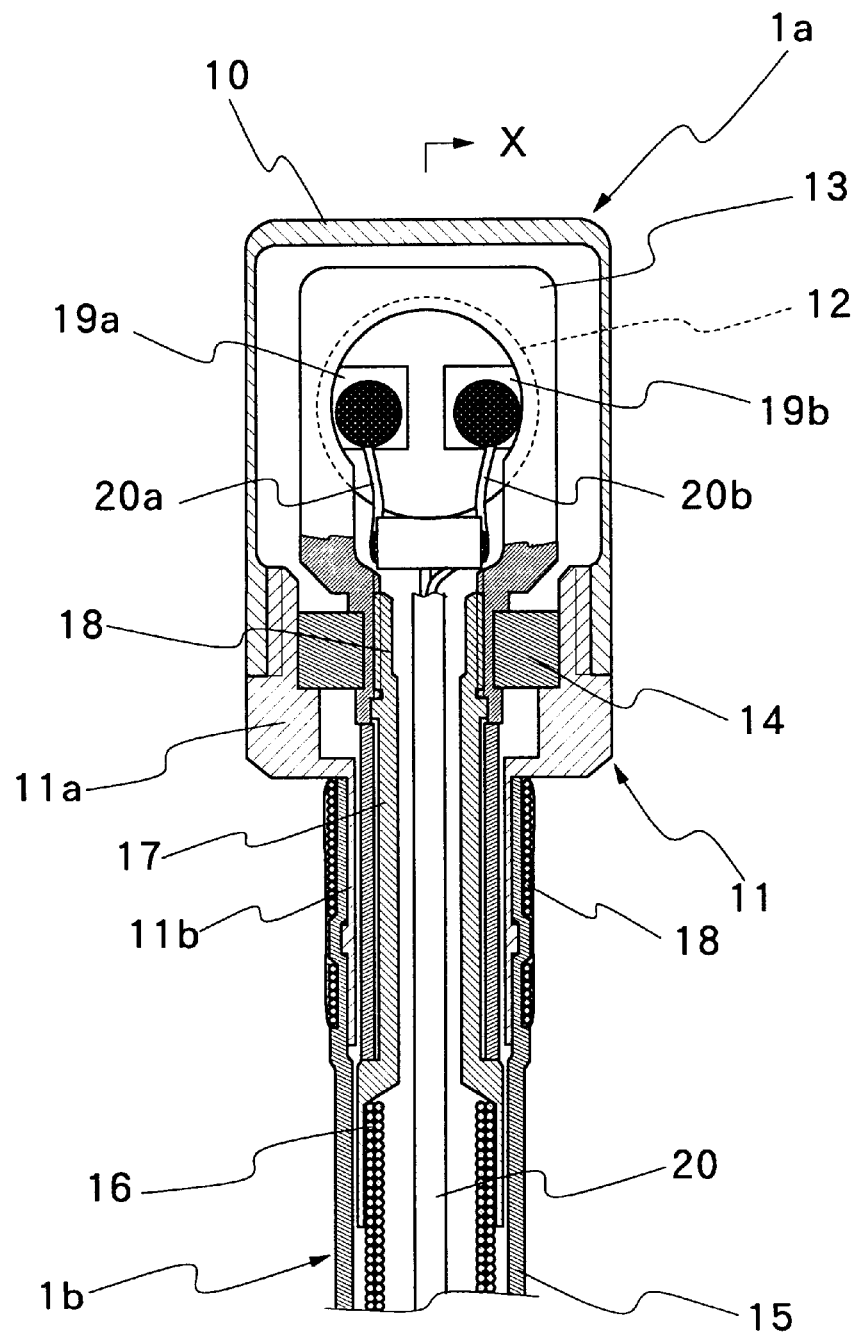
FIG. 3 is a longitudinal sectional view of a fore end portion of the ultrasound probe.
Figure 4:
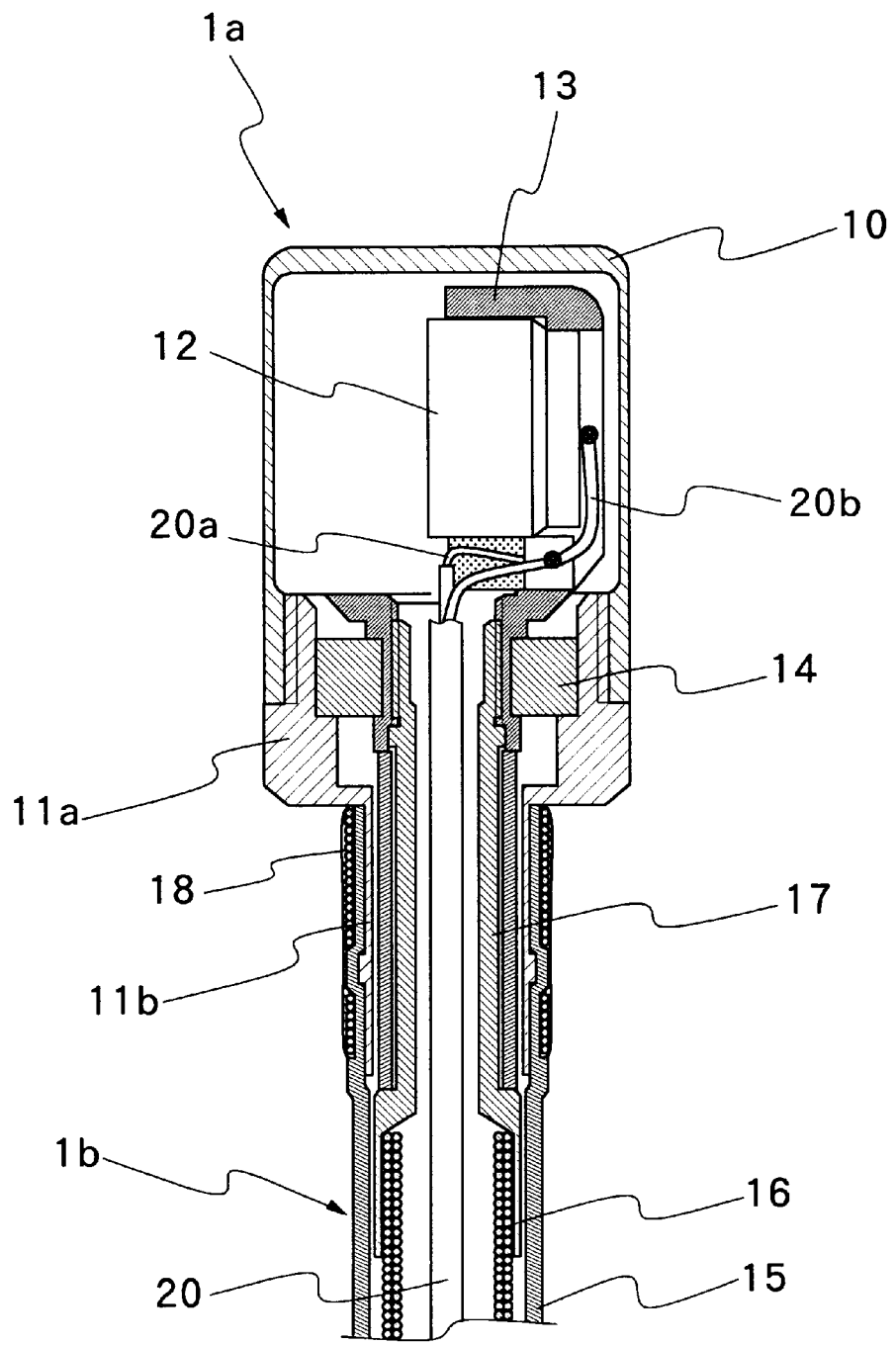
FIG. 4 is a schematic sectional view taken on line X—X of FIG. 3.

Shown in FIGS. 2 through 5 is the construction of the ultrasound probe 1. Firstly, as shown in FIG. 2, the ultrasound probe 1 includes, from its fore end, an ultrasound scanner head 1a, a flexible cord 1b and a tail end connector 1c. The ultrasound scanner head 1a is far larger in outside diameter than the flexible cord 1b and the tail end connector 1c, which are smaller than the inside diameter of the endoscopic biopsy channel 9. As shown particularly in FIGS. 3 and 4, the ultrasound scanner head 1a is encased in an end cap 10 which is formed, for example, of silicon resin, polyethylene or other synthetic resins with satisfactory properties in ultrasound transmission, and which is relatively thin in wall thickness. The ultrasound scanner head 1a is joined with the fore end of the flexible cord 1b through a joint member 11 of rigid metal which is connected to the end cap 10 for the purpose of retaining the shape of the end cap 10 and at the same time for augmenting the strength of its joint portion with the flexible cord 1b. In the particular embodiment shown, the joint member 1 is in the form of a stepped cylinder with large- and small-diameter portions 11a and 11b at its front and rear ends to be connected with the end cap 10 and the flexible cord 1b which correspondingly have small and large diameters, respectively. Accordingly, the joint member 11 has a radial step-like surface at the border between the front or larger joint portion 11a on the side of the end cap 10 and the rear or smaller joint portion 11b on the side of the flexible cord 1b, perpendicularly to the axis of the ultrasound scanner head 1a.

An ultrasound transducer element for radial scan is mounted on a rotary base 13 within the end cap 10. The rotary base 13 is rotatably supported in a bearing 14 which is fitted in the end cap 10. Both the rotary base 13 and the bearing 14 are formed of an electrically insulating synthetic resin material. Especially, the bearing 14 is formed of a low-friction synthetic resin like fluororesin. The end cap 10 and the front joint portion 11a of the joint member 11 are formed in a larger diameter than the endoscopic biopsy channel 9 for the purpose of broadening the internal space of the end cap 10. As a consequence, the end cap 10 of the ultrasound scanner head 1a can accommodate a large-size ultrasound transducer element 12 with a broader active surface which is advantageous in scanning targets in deep positions.

The flexible cord 1b has a flexible transmission shaft 16 fitted in an outer tube 15 which is formed of a soft and flexible synthetic resin material. The flexible transmission shaft 16 is constituted by a tube of tightly wound metal wire coils. In order to transmit rotation efficiently from the flexible shaft 16 to the rotary base 13 which supports the ultrasound transducer element 12, it is preferred that the flexible shaft 16 is constituted by a double coil tube. Since the rotary base 13 is formed of a synthetic resin material, it is difficult to form a strong joint when the flexible transmission shaft 16 is directly connected to the rotary base 13. Therefore, the fore end of the flexible transmission shaft 16 is securely fixed, for example, by welding, soldering or brazing, to a cylindrical rotating member 17 of rigid metal which has its fore end threaded into the rotary base 13. On the other hand, the fore end of the outer sheathing tube 15 is fitted on the rear joint portion 11b of the joint member 11 over a suitable length and bonded to the latter by the use of an adhesive. In addition to the bonding by an adhesive, the outer tube 15 is securely fastened to the rear joint portion 11b of the joint member 11 by line wrapping 18. The rear joint portion 11b of the joint member 11 has a length which is determined on the basis of the strength of the fitting joint with the outer tube 15. In the particular embodiment shown, the rear joint portion 11b is elongated to some extent for the purpose of increasing the strength of the joint with the outer tube 15.

The ultrasound transducer element 12 is provided with a pair of electrodes 19a and 19b which are connected with signal lines 20a and 20b of a coaxial cable 20 passed through the cylindrical rotating member 17. The coaxial cable 20 is passed internally through the flexible transmission shaft 16 and extended as far as the tail end connector 1c of the probe 1.

Figure 5:
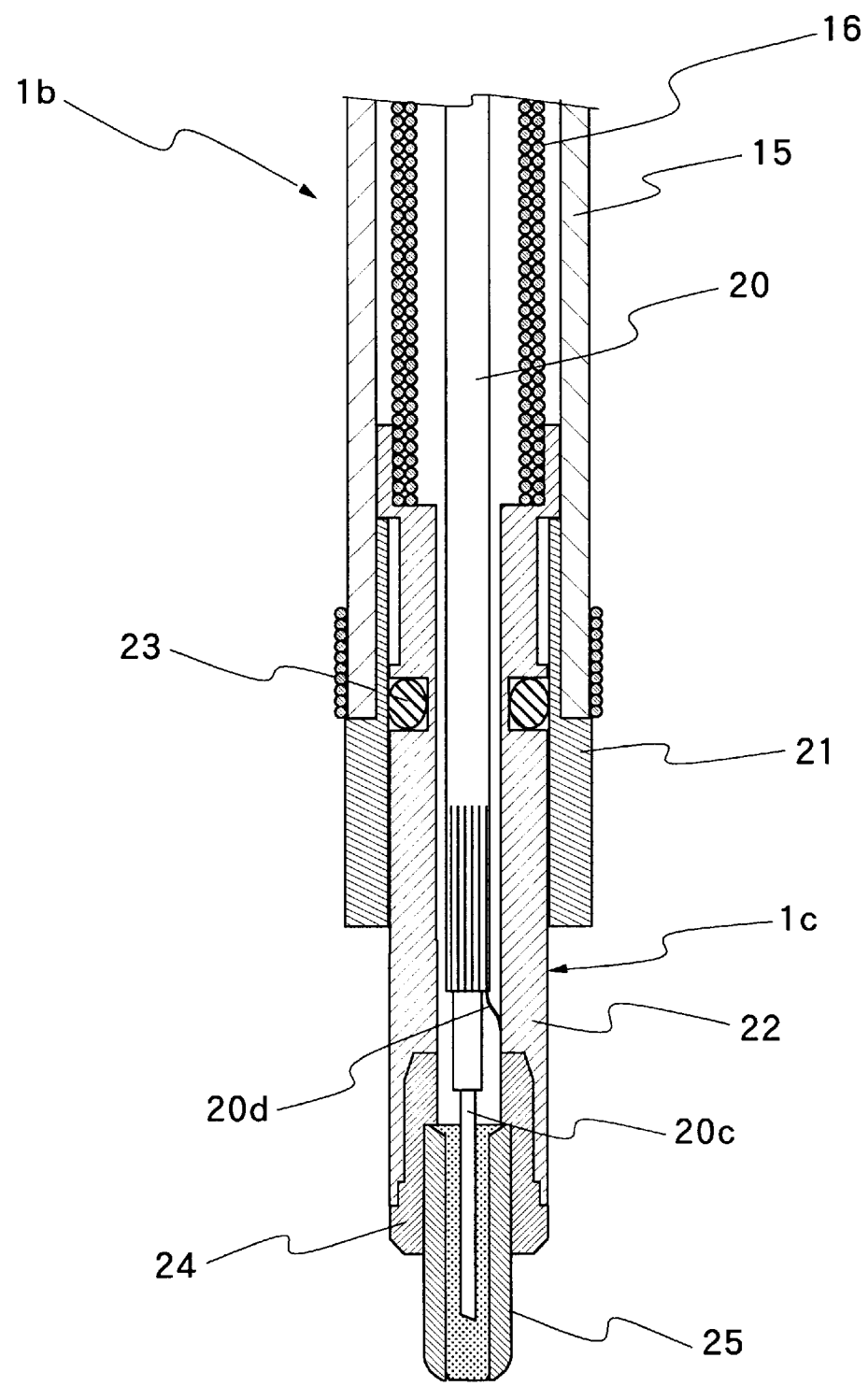
FIG. 5 is a longitudinal sectional view of a proximal end portion of the ultrasound probe.

Shown in section in FIG. 5 is a joint portion of the flexible cord 1b and the tail end connector 1c. The tail end connector 1c is constituted by stationary member and rotating parts. The stationary part includes a rigid metal pipe 21, and a proximal end portion of the outer tube 15 is fitted on and securely fixed to this metal pipe 21. For example, the rigid metal pipe 21 is formed in a polygonal shape on the outer peripheral side and in a circular shape on the inner peripheral side, and fixedly connectible to a stationary cylindrical member on the part of the probe controller 2. The rotating part includes a cylindrical rotating member 22 of rigid metal, which is securely fixed with the proximal end of the flexible transmission shaft 16 by welding or by other suitable fixation method. This rotating member 22 is partly fitted in the rigid stationary pipe 21 for rotational movements in and relative to the latter. A seal member 23 is interposed between the rotating member 22 and the rigid stationary member 21 which are in sliding contact with each other, thereby hermetically sealing the tail end connector 1c from outside. The proximal end portion of the rotating member 22, which is projected to the outside from the stationary pipe 21, is provided with a chamfered surface so that it can be rotated integrally with a rotational shaft on the probe controller 2 when coupled with the latter. Further, an insulating support member 24 is fixedly fitted in the projected end of the rotating member 22 to hold an electrode pin 25 therein.

The metallic rotating member 22 and the electrode pin 25 serve as electrodes to be disconnectibly connected to corresponding electrodes on the part of the probe controller 2, and are connected with the shield and core wires 29d and 20c of the coaxial cable 20 which is passed through the flexible transmission shaft 16 as mentioned hereinbefore. The rotating member 22 which functions as an electrode is directly connected with the flexible transmission shaft 16, that is, rotationally directly coupled with the latter. The opposite front end of the flexible transmission shaft 16 is connected to the aforementioned rotary ring 17 which is also formed of a metallic material. Consequently, when the tail end connector 1c is plugged into the probe controller 2 which is connected with the ultrasound image observation terminal 3, current flows to the rotating member 22 upon turning on a power switch of the ultrasound image observation terminal 3, holding the flexible transmission shaft 16 and the rotary ring 17 at the same potential. Therefore, if either the flexible transmission shaft 16 or rotary ring 17 should come into contact with the rear joint portion 11b of the joint member 11 within a body cavity, electric current would flow into the patient's body.

Figure 6:
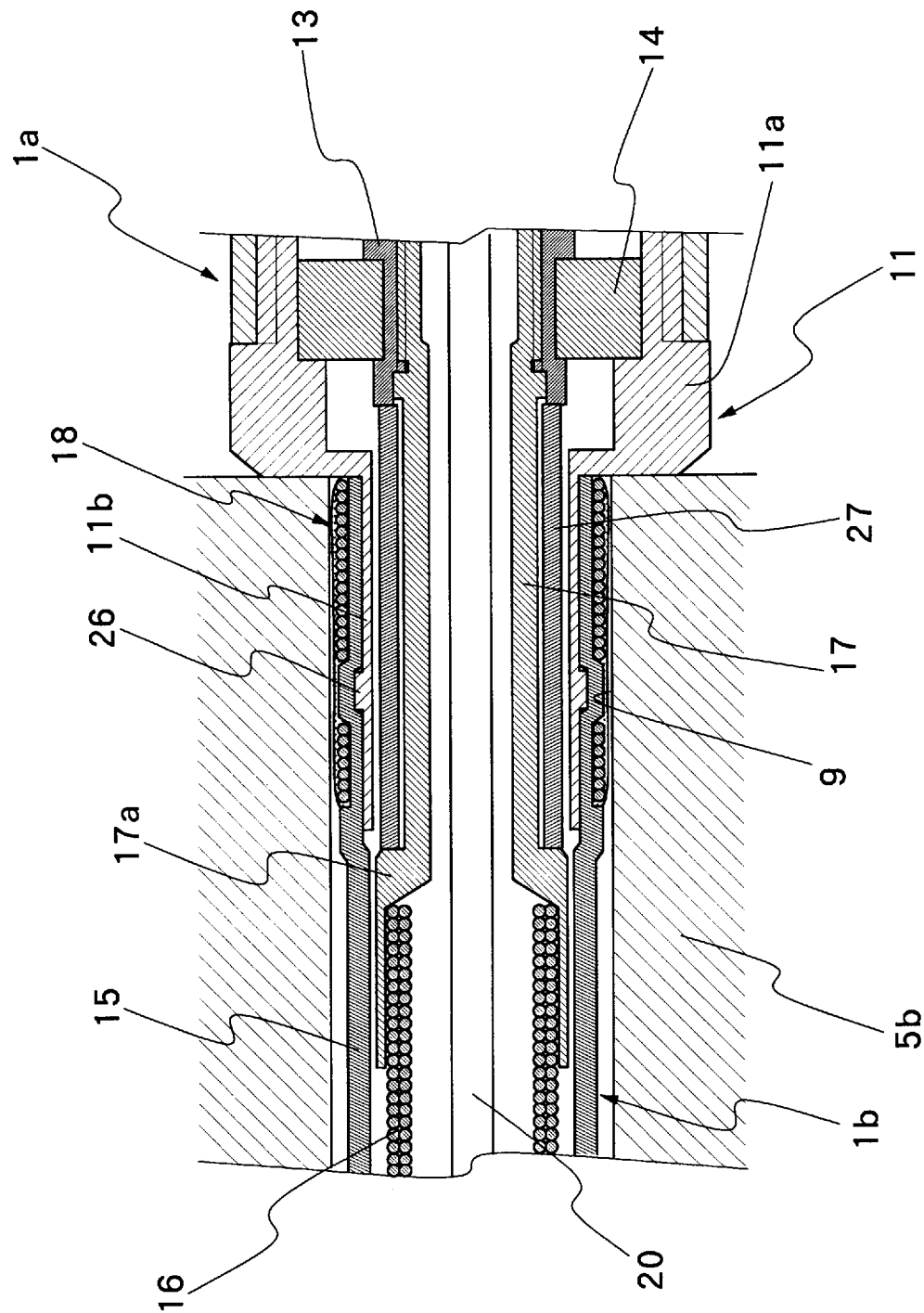
FIG. 6 is a longitudinal section through a joint portion of an ultrasound scanner head and a flexible cord of the probe.

In order to avoid this, the joint member 11 should be maintained out of contact with both of the flexible transmission shaft 16 and the rotary ring 17 by employing a joint construction as shown in FIG. 6 for the ultrasound scanner head 1a and the flexible cord 1b.

In the joint construction of FIG. 6, firstly the cylindrical rotating member 17 is extended beyond the proximal end of the rear joint portion 11b of the joint member 11 and, at that extended position, connected with the fore end of the flexible transmission shaft 16. Accordingly, the probe 1 has a rigid fore end section extending axially from the distal end of the ultrasound scanner head 1a to the proximal end of the cylindrical rotating member 17. In this instance, of the various parts of the ultrasound probe 1, the flexible cord 1b and the tail end connector 1c are passed through the endoscopic biopsy channel 9, while the ultrasound scanner head 1a is projected from and always remains outside the biopsy channel 9. Accordingly, of the rigid fore end portion of the ultrasound probe 1, it is from the rear joint portion 11b of the joint member 11 to the proximal end of the cylindrical rotating member 17 that are located within the endoscopic biopsy channel 9.

On the other hand, the insertion instrument 7 of the endoscope 5 is also provided with a rigid tip end section 7c. It follows that the flexible cord 1b of the ultrasound probe 1 which is placed in the endoscopic biopsy channel 9 is not necessarily required to have flexibility in those portions which are located within the rigid tip end section 7c of the endoscopic insertion instrument 7, more specifically, in those portions which are located forward of an end ring (not shown) which connects the rigid tip end section 7c with the angle section 7b of the endoscopic insertion instrument 7. The rigid tip end section 7c needs to have a certain axial length in order to accommodate endoscopic image pickup means including the objective lens and solid-state image sensor as mentioned hereinbefore. Therefore, the length of a rigid fore end portion of the ultrasound probe 1 to be located in the endoscopic biopsy channel 9 should not exceed the length of the rigid tip end section of the endoscopic insertion instrument 7. When the probe is arranged in this manner, it becomes possible to extend the cylindrical rotating member 17 to a point on the proximal side of the inner end of the rear joint portion 11b of the joint member 11, while securing a necessary strength for joint portions of the rear joint portion 11b and the outer tube 15.

In this instance, despite a reduction in length of the fitting engagement of the outer tube 15 with the rear joint portion 11b of the joint member 11, these parts are joined with each other with a sufficient strength. Namely, the rear joint portion 11b of the joint member 11 is formed with an annular protuberance 26 therearound in an axially intermediate position, and a fore end portion of the outer tube 15 is forcibly fitted over and beyond the annular protuberance 26 up to a position where it meets the radial stepped surface between the front and rear joint portions 11a and 11b of the joint member 11. In addition, line wrappings 18 are formed around the outer tube 15 on the front and rear sides of the annular protuberance 26 thereby to restrict axial displacements of the tube 15 on the joint member 11 completely despite the reduction in length of fitting engagement.

No matter whether or not the joint strength is augmented in the above-described manner, in order to preclude the possibilities of contact between the flexible shaft 16 and the rear joint portion 11b of the joint member 11, the length of a rigid fore end portion of the ultrasound probe 1 should not exceed the length of the rigid tip end section of the endoscopic insertion instrument 7, and the position of the joint portion of the cylindrical rotating member 17 with the flexible transmission shaft 16 should be located to the proximal side of the inner end of the rear joint portion 11b. Since the rear joint portion 11b of the joint member 11 is maintained in a fixed state even when the flexible transmission shaft 16 is in rotation, direct contact of the rear joint portion 11b with the rotating flexible shaft 16 would cause not only the trouble of electrical conduction but also contamination of an ultrasound transmission medium, which is sealed internally of the probe, with abraded particles from sliding portions. Therefore, keeping the flexible transmission shaft 16 and rear joint portion 11b of the joint member 11 completely from contact with each other is extremely advantageous from the standpoint of preventing occurrence of abraded particles by sliding contact, in addition to the prevention of electrical conduction between them.

While the flexible shaft 16 is completely kept out of contact with the joint member 11 by the above-described arrangements, the cylindrical rotating member 17 which is passed internally of the rear joint portion 11b should also be kept out of contact with the latter. For this purpose, an insulating sleeve 27 is fitted on the cylindrical rotating member 17. The insulating sleeve 27 is fixedly held in position by and between a radial wall at the outer end of a large diameter portion 17a, which is formed on the cylindrical rotating member 17 to receive the outer end of the flexible transmission shaft 16, and an inner end face of the rotary base 13. Thus, the rear joint portion 11b is confronted by the insulating sleeve 27 along its entire axial length and thereby securely kept out of contact with the cylindrical rotating member 17. Consequently, the rear joint portion 16 is always kept out of contact with both the flexible shaft 16 and the cylindrical rotating member, completely precluding the possibilities of current conduction to the patient's body while the rotary base 13 is rotationally driven through the flexible transmission shaft 16 to transmit and receive ultrasound signals through the ultrasound transducer element which is supported on the rotary base 13.

There are no restrictions in particular with regard to the material for the insulating sleeve 27 as long as it has satisfactory properties in electrical insulation. At the time of an ultrasound scanning operation, this insulating sleeve 27 is put in rotation while the opposing rear joint portion 11b of the joint member 11 remains in a standstill state. Accordingly, the insulating sleeve 27 can be held in sliding contact with the rear joint portion 11b due to radial drifting of the rotational axis of the latter. Considering the possibilities of such sliding contact, the insulating sleeve 27 is preferred to be formed of a low-friction insulating material such as Teflon and Delrin (trade names for products of E. I. du Pont de Nemours & Co. Inc.).

The ultrasound probe 1, which is arranged in the above-described manner, is placed in the endoscope 5 as shown in FIG. 1 prior to introduction into a body cavity. The ultrasound probe 1 is placed in the endoscopic biopsy channel 9 inversely from tail to head, that is, from the tail end connector 1c through an opening at the distal end of the endoscopic insertion instrument 7, and the tail end connector 1c at the leading end of the probe 1 is drawn out through the entrance housing 8 and connected to the probe controller 2. Nextly, in order to stabilize the ultrasound scanner head 1a which projects from the distal end of the endoscopic insertion instrument 7, a tensile force is applied to the flexible cord 1b so that the ultrasound scanner head 1a is pulled toward and abutted against marginal edges around the front opening of the endoscopic biopsy channel 9. Once stabilized in this manner, the ultrasound scanner head 1a would not obstruct the movement of the endoscopic insertion instrument 7 at the time of introduction into a body cavity. Besides, it becomes possible to locate the ultrasound scanner head 1a accurately in a desired position by angling operations of the angle section 7b.

For an ultrasound scan, the rotary base 13 which supports the ultrasound transducer element 12 is put in rotation by remote control, that is, by actuating the rotational drive means on the probe controller 2 to rotate the flexible transmission shaft 16 about its longitudinal axis within the outer tube 15, and at the same time trigger pulses are applied to the ultrasound transducer element 12 from the ultrasound image observation terminal 3 to transmit ultrasound pulses into the patient's body at predetermined angular intervals. In receiving return echo signals, the ultrasound transducer element 12 which is of a large size is very advantageous, particularly for ultrasound examinations at deep positions. Besides, in addition to improvements in strength, it becomes possible to make the construction of the tail end connector 1c simpler and to reduce its axial length, since the connector 1c is constituted simply by the cylindrical rotating member 22 which is connected to the proximal end of the flexible transmission shaft 16, and the electrode pin 25 which is supported on the insulating support member 24 at the fore end of the rotating member 22. This means that the tail end connector 1c which forms a rigid portion can be easily passed through the endoscopic biopsy channel 9.

As described hereinbefore, for the purpose of simplifying the construction of the tail end connector 1c, the cylindrical rotating member 22 which is directly connected with the flexible transmission shaft 16 is used as an electrode. Nevertheless, there is no possibility of electric current flowing into a patient's body since the metallic joint member 11 which is provided in an exposed state on the ultrasound scanner head 1a for connection with the flexible cord 1b is always maintained out of contact with both of the flexible shaft 16 and the cylindrical rotating member 17.

What is claimed is:

1. An ultrasound probe of the type having, successively from head to tail end thereof, an ultrasound scanner head assembly accommodating an ultrasound transducer element rotatably within an end cap, an elongated flexible cord having a flexible transmission shaft of tightly wound metal wire coils within an outer sheathing tube, and a tail end connector, said ultrasound probe comprising:

a metallic joint member axially extended from said end cap of said ultrasound scanner head assembly on the proximal side thereof and joining said ultrasound scanner head with a fore end portion of said outer sheathing tube of said flexible cord by fitting engagement therewith;

a cylindrical rotating member located internally of said joint member and said outer sheathing tube, and connecting a fore end portion of said flexible transmission shaft with a rotary support member of said ultrasound transducer element at a position axially on the proximal side of a rear end of said joint member; and an insulating sleeve member fitted on said cylindrical rotating member and keeping said cylindrical rotating member out of contact with said metallic joint member for electrical insulation purposes.

2. An ultrasound probe as defined in claim 1, wherein said insulating sleeve is formed of a low-friction synthetic resin material.

3. An ultrasound probe as defined in claim 1, wherein said flexible cord and said tail end connector are formed in a diameter which is passable through a biopsy channel in an elongated insertion instrument of an endoscope, and said ultrasound scanner head is formed in a bulky shape larger than an inside diameter of said endoscopic biopsy channel.

4. An ultrasound probe as defined in claim 3, wherein said joint member and said outer tube of said flexible cord are joined by fitting engagement over a length which falls within a length of a rigid fore tip end section of said endoscopic insertion instrument when said ultrasound probe is placed in said endoscopic biopsy channel with said ultrasound scanner head projected through a front opening of said biopsy channel.

* * * * *